United States Patent [19]

Riebel et al.

[11] Patent Number: 4,734,427

[45] Date of Patent: Mar. 29, 1988

[54] FUNGICIDAL PHENYLSULPHONYL IMIDAZOLES

[75] Inventors: Hans-Jochem Riebel, Wuppertal, Fed. Rep. of Germany; Akihiko Yanagi, Tokyo, Japan; Akinori Hirashima, Wuppertal, Fed. Rep. of Germany; Wilhelm Brandes, Leichlingen, Fed. Rep. of Germany; Paul Reinecke, Leverkusen, Fed. Rep. of Germany

[73] Assignee: Bayer Aktiengesellschaft, Leverkusen, Fed. Rep. of Germany

[21] Appl. No.: 12,988

[22] Filed: Feb. 10, 1987

[30] Foreign Application Priority Data

Feb. 22, 1986 [DE] Fed. Rep. of Germany ....... 3605714

[51] Int. Cl.$^4$ .................... A01N 43/50; C07D 233/56
[52] U.S. Cl. .................... 514/398; 514/359; 548/337
[58] Field of Search ................. 514/359, 398; 548/337

[56] References Cited

U.S. PATENT DOCUMENTS 4,115,060 9/1978 Finley et al. ........................ 8/111

FOREIGN PATENT DOCUMENTS 1198995 10/1959 France ................. 514/359

OTHER PUBLICATIONS

*Chemical Abstracts,* vol. 85: 6299bt (1976) [Mikhailova, V., et al., *2H. Obshch Khim.* 1976, 46(4), 879–880].
*Chemical Abstracts,* vol. 63:(8344c(1965)[Feldman, I., et al., *2H Obshch Khim.* 35(1), 186–188(1965)].

*Primary Examiner*—Richard A. Schwartz
*Attorney, Agent, or Firm*—Sprung Horn Kramer & Woods

[57] ABSTRACT

The phenylsulphonylazoles of the formula

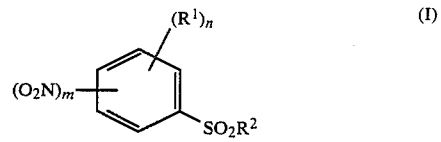

in which
$R^1$ represents alkyl,
m represents the number 1 or 2,
n represents the number 0 or 1, and
$R^2$ represents a radical of the formula

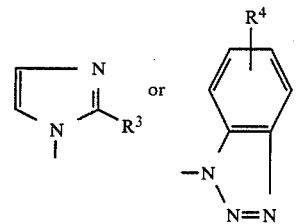

wherein
$R^3$ represents alkyl, and
$R^4$ represents hydrogen, halogen, nitro or alkyl.

are particularly suitable for combating undesirable microorganisms.

10 Claims, No Drawings

FUNGICIDAL PHENYLSULPHONYL IMIDAZOLES

The present invention relates to microbicidal compositions and to methods for combating undesirable microorganisms, such as fungi, using certain phenylsulphonylazoles, some of which are known. The invention also relates to certain novel phenylsulphonylazoles.

It is already known that certain phenylsulphonylimidazoles can be used as bleaching agents (compare U.S. Pat. No. 4,115,060). Thus, for example, 1-(4-methylphenylsulphonyl)-imidazole can be used for cleaning and brightening textiles.

It is furthermore known that certain N-halogenoalkylthioimides have fungicidal properties (compare EP-OS (European Published Specification) No. 0,044,394). Thus, for example, N-trichloromethylthio-tetrahydrophthalimide can be used for combating fungi. However, the action of this substance is not always completely satisfactory when low amounts are applied.

Certain phenylsulphonylbenzotriazoles have furthermore already been described (compare Chem. Abstr. 63, 8344 c (1965) and Chem. Abstr. 85, 62 996 t). However, biological properties of these substances are hitherto unknown.

It has now been found that the phenylsulphonylazoles of the formula

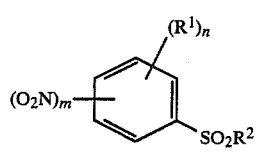

in which
$R^1$ represents alkyl,
m represents the number 1 or 2,
n represents the number 0 or 1, and
$R^2$ represents a radical of the formula

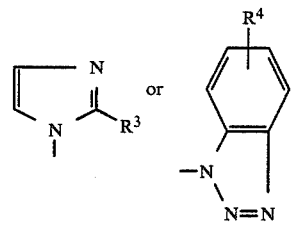

wherein
$R^3$ represents alkyl and
$R^4$ represents hydrogen, halogen, nitro or alkyl, are particularly suitable for use as microbicides.

Surprisingly, the phenylsulphonylazoles of the formula (I) which can be used according to the invention have a better fungicidal activity than N-trichloromethylthio-tetrahydrophthalimide, which is a structurally similar already known active compound of the same type of action. The phenylsulphonylazoles of the formula (I) are moreover also superior to the known compound 1-(4-methylphenylsulphonyl)-imidazole in respect of fungicidal properties.

Formula (I) provides a general definition of the phenylsulphonylazoles which can be used according to the invention. Preferably, in this formula, $R^1$ represents alkyl with 1 to 6 carbon atoms,
m represents the numbers 1 and 2,
n represents the numbers 0 and 1, and
$R^2$ represents a radical of the formula

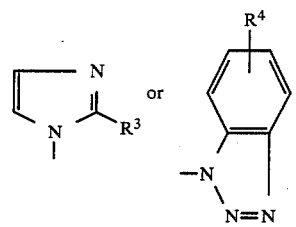

wherein
$R^3$ represents alkyl with 1 to 4 carbon atoms, and
$R^4$ represents hydrogen, fluorine, chlorine, bromine or nitro, or represents alkyl with 1 to 4 carbon atoms.

Compounds of the formula (I) which can particularly preferably be used are those
in which
$R^1$ represents alkyl with 1 to 4 carbon atoms,
m represents the numbers 1 and 2,
n represents the numbers 0 and 1, and
$R^2$ represents a radical of the formula

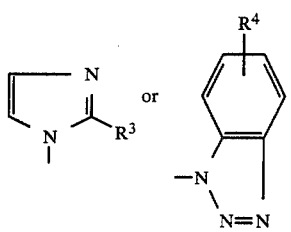

wherein
$R^3$ represents methyl or ethyl, and
$R^4$ represents hydrogen, fluorine, chlorine, bromine, methyl, ethyl, n-propyl, i-propyl or nitro.

Compounds which can especially preferably be used are those
in which
$R^1$ represents methyl, ethyl or n-propyl,
m represents the numbers 1 and 2,
n represents the numbers 0 and 1, and
$R^2$ represents a radical of the formula

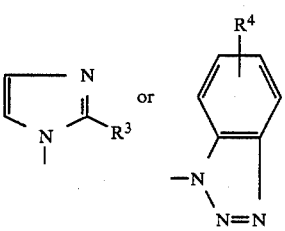

wherein
$R^3$ represents methyl, and
$R^4$ represents hydrogen, chlorine, nitro or methyl.

Of particular importance are the compounds of the formula

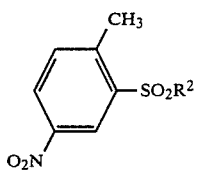

in which

R² represents a radical of the formula

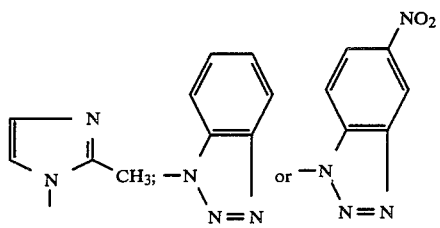

The phenylsulphonylazoles of the formula (I) which can be used according to the invention are known in some cases (compare Chem. Abstr. 63, 8344 c (1965) and Chem. Abstr. 85, 62 996 t).

The phenylsulphonylazoles of the formula

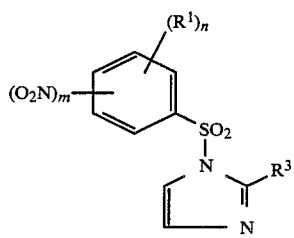

in which
R¹ represents alkyl,
m represents the numbers 1 or 2,
n represents the numbers 0 or 1, and
R³ represents alkyl,
are new.

The phenylsulphonylazoles of the formula (Ib) can be prepared by a process in which sulphonyl halides of the formula

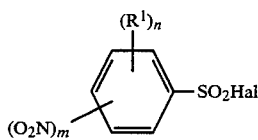

in which
R¹, m and n have the abovementioned meanings and
Hal represents halogen,
are reacted with imidazole derivatives of the formula

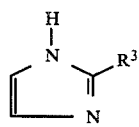

in which

R³ has the abovementioned meaning,
if appropriate in the presence of an acid acceptor and if appropriate in the presence of a diluent.

Formula (Ib) provides a general definition of the new phenylsulphonylazoles. In this formula, R¹, R³, m and n preferably have those meanings which have already been mentioned as preferred for these radicals and these indices in connection with the description of the phenylsulphonylazoles of the formula (I) which can be used according to the invention.

If, for example, 4-methyl-3-nitro-benzenesulphonyl chloride and 2-methylimidazole are used as starting substances, the course of the reaction in the process described above can be represented by the following equation:

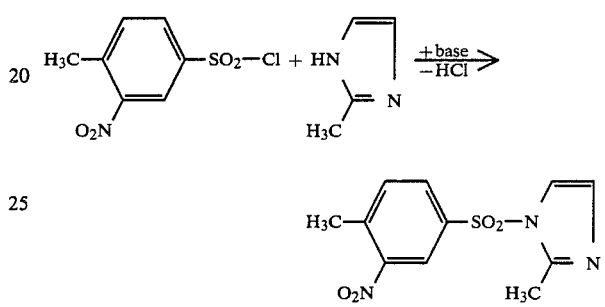

Formula (II) provides a general definition of the sulphonyl halides to be used as starting substances in carrying out the process described above. In this formula, R¹, m and n preferably have those meanings which have already been mentioned as preferred for the radical R¹ and the indices m and n in connection with the description of the substances of the formula (I) which can be used according to the invention. Hal preferably represents chlorine or bromine.

Examples which may be mentioned of the compounds of the formula (II) are: 2-nitro-, 3-nitro-, 4-nitro-, 2-methyl-3-nitro-, 4-methyl-3-nitro-, 2-methyl-5-nitro-, 3,5-dinitro-2-methyl-, 2-methyl-4-nitro-, 2-ethyl-5-nitro-, 2-n-propyl-5-nitro-, 2-iso-propyl-5-nitro- and 2-n-butyl-5-nitro-benzenesulphonyl chloride and bromide.

The compounds of the formula (II) are known compounds of organic chemistry or can be prepared by generally known processes.

Formula (III) provides a general definition of the imidazole derivatives which are also to be used as starting substances in the process described above. In this formula, R³ preferably has those meanings which have already been mentioned as preferred for this substituent in connection with the description of the substances of the formula (I) which can be used according to the invention.

Examples which may be mentioned of the compounds of the formula (III) are: 2-methyl-, 2-ethyl-, 2-n-propyl-, 2-i-propyl-, 2-n-butyl-, 2-i-butyl-, 2-sec.-butyl- and 2-tert.-butyl-imidazole.

The imidazole derivatives of the formula (III) are known compounds of organic chemistry or can be prepared by generally known processes.

The process for the preparation of the new phenylsulphonylazoles of the formula (Ib) is preferably carried out using diluents. Possible diluents here are virtually all the inert organic solvents. These include, preferably, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as dimethyl ether, dibutyl ether, glycol dimethyl ether, diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, and pyridine.

Acid acceptors which can be used in the process described above are all the acid-binding agents which can usually be employed for such reactions. Preferred possible acid-binding agents are alkali metal carbonates, such as sodium carbonate and potassium carbonate, and furthermore aliphatic, aromatic or heterocyclic amines, for example triethylamine, trimethylamine, dimethylaniline, dimethylbenzylamine, pyridine, 1,5-diazabicyclo-[4,3,0]-non-5-ene (DBN), 1,8-diazabicyclo-[5,4,0]-undec-7-ene (DBU) and 1,4-diazabicyclo-[2,2,2]-octane (DABCO).

The reaction temperatures can be varied within a substantial range in the process described above. The reaction is in general carried out at temperatures between $-30°$ C. and $+100°$ C., preferably at temperatures between $-20°$ C. and $+60°$ C.

The process described above is in general carried out under normal pressure. However, it is also possible for it to be carried out under increased or reduced pressure.

For carrying out the process described above, the particular starting substances required are in general employed in approximately equimolar amounts. However, it is also possible for one of the two particular components employed to be used in a relatively large excess. The reactions are in general carried out in a suitable diluent in the presence of an acid acceptor, and the reaction mixture is stirred at the particular temperature required for several hours.

The reaction products are isolated by customary methods. Thus, a procedure is in general followed in which the reaction mixtures are poured into water and the products which have precipitated are filtered off. However, it is also possible to wash the reaction mixture with dilute acid and water and to concentrate the organic phase which remains.

Not only the phenylsulphonylazoles of the formula (Ib) but also the other substances of the formula (I) can be prepared by the process described above.

The active compounds which can be used according to the invention have a powerful microbicidal action and can be employed in practice for combating undesirable microorganisms. The active compounds are suitable, above all, for use as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation: Pythium species, such as, for example, *Pythium ultimum;* Phytophthora species, such as, for example, *Phytophthora infestans;* Pseudoperonospora species, such as, for example, *Pseudoperonospora humuli* or *Pseudoperonospora cubense;* Plasmopara species, such as, for example, *Plasmopara viticola;* Peronospora species, such as, for example, *Peronospora pisi* or *P. brassicae;* Erysiphe species, such as, for example, *Erysiphe graminis;* Sphaerotheca species, such as, for example, *Sphaerotheca fuliginea;* Podosphaera species, such as, for example, *Podosphaera leucotricha;* Venturia species, such as, for example, *Venturia inaequalis;* Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus;* Puccinia species, such as, for example, *Puccinia recondita;* Tilletia species, such as, for example, *Tilletia caries;* Ustilago species, such as, for example, *Ustilago nuda* or *Ustilago avenae;* Pellicularia species, such as, for example, *Pellicularia sasakii;* Pyricularia species, such as, for example, *Pyricularia oryzae;* Fusarium species, such as, for example, *Fusarium culmorum;* Botrytis species, such as, for example, *Botrytis cinerea;* Septoria species, such as, for example, *Septoria nodorum;* Leptosphaeria species, such as, for example, *Leptosphaeria nodorum;* Cercospora species, such as, for example, *Cercospora canescens;* Alternaria species, such as, for example, *Alternaria brassicae* and Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and furthermore in formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene-fatty acid esters, polyoxyethylene-fatty alcohol etherss, for example alkylaryl polyglycol ether, alkyl sulphonates, alkyl sulphates, aryl sulphonates as well as albumin hydrolysis products. As dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospho-lipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds which can be used according to the invention can be present in the formulations as a mixture with other known active compounds, such as fungicides, insecticides, acaricides and herbicides, and in mixtures with fertilizers and growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering dusting, foaming, brushing on and the like. It is furthermore possible to apply the active compounds by the ultra-low volume method or to inject the active compound formulation or the active compound itself into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

The preparation of phenylsulphonylazoles of the formula (I) is illustrated by the following examples.

PREPARATION EXAMPLES

Example 1

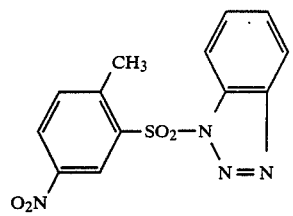

11.8 g (0.05 mol) of 2-methyl-5-nitro-benzenesulphonyl chloride are added drowise to a solution of 5.95 g (0.05 mol) of benzotriazole in 75 ml of pyridine at 20° to 25° C. and the mixture is subsequently stirred at 50° C. for 3 hours. After cooling, the reaction mixture is poured onto 500 ml of water and extracted three times with 50 ml of chloroform each time. The organic phases are combined, washed twice with 300 ml of water each time and then dried and concentrated. The residue is recrystallized from toluene.

5.8 g (36.5% of theory) of 1-(2-methyl-5-nitrophenylsulphonyl)-benzotriazole are obtained as colorless crystals of melting point 169° to 170° C.

Example 2

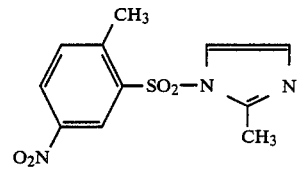

235.5 g (1 mol) of 2-methyl-5-nitro-benzenesulphonyl chloride in 500 ml of methylene chloride are added dropwise to a solution of 82 g (1 mol) of 2-methylimidazole and 135 g (1.2 mol) of 1,4-diazabicyclo-[2,2,2]-octane (DABCO) in 2 l of methylene chloride at −20° C. and the mixture is subsequently stirred at 20° to 25° C. for 3 hours. The reaction mixture is then washed with dilute hydrochloric acid and water and concentrated and the residue is recrystallized from acetonitrile.

180 g (64% of theory) of 2-methyl-1-(2-methyl-5-nitro-phenylsulphonyl)-imidazole are obtained as colorless crystals of melting point 159° C.–161° C.

The following compounds of the general formula

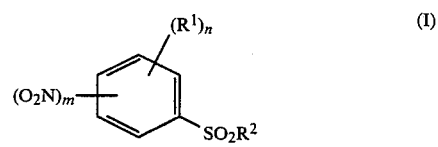

can be prepared analogously to Example 1 and 2:

TABLE 1

| Example No. | ![ring with (O2N)m and (R1)n] | R² | Melting point [°C.] |
|---|---|---|---|
| 3 | 4-H3C, 3-O2N phenyl | -N=C(CH3)-N (imidazoline) | |
| 4 | 2,4-(O2N)2, 3-CH3 phenyl | -N=C(CH3)-N (imidazoline) | |
| 5 | 2-NO2 phenyl | -N=C(CH3)-N (imidazoline) | 131 |
| 6 | 3-O2N phenyl | -N=C(CH3)-N (imidazoline) | 156 |
| 7 | 4-O2N phenyl | -N=C(CH3)-N (imidazoline) | 136 |
| 8 | 4-H3C, 3-O2N phenyl | -N(N=N)-phenyl (benzotriazole) | |
| 9 | 2,4-(O2N)2, 3-CH3 phenyl | -N(N=N)-phenyl (benzotriazole) | |
| 10 | 2-NO2 phenyl | -N(N=N)-phenyl (benzotriazole) | 144 |
| 11 | 3-O2N phenyl | -N(N=N)-phenyl (benzotriazole) | 99–100 |
| 12 | 4-O2N phenyl | -N(N=N)-phenyl (benzotriazole) | |
| 13 | 4-O2N, 3-CH3 phenyl | 2-NO2 benzotriazole | 168–169 |
| 14 | 4-O2N phenyl | 2-NO2 benzotriazole | 174 (decomposition) |
| 15 | 3-O2N phenyl | 4-NO2 benzotriazole | 164–168 |

Example A

Phytophthora test (tomato)/protective
Solvent: 4.7 parts by weight of acetone
Emulsifier: 0.3 parts by weight of alklylarylpolyglycolether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of *Phytophthora infestans.*

The plants are placed in an incubation cabinet at 100% relative atmospheric humidity and at about 20° C.

Evaluation is carried out 3 days after the inoculation.

The active compounds, active compound concentrations and results can be seen from the following table.

TABLE A

Phytophthora test (tomato)/protective

| Active compound | Infestation in % at an active compound concentration of 10 ppm |
|---|---|
| known: | |
| ![structure A] | 23 |
| According to the invention: | |
| (1) | 10 |
| (2) | 6 |

Example B

Phytophthora test (tomato)/curative

Solvent: 4.7 parts by weight of acetone

Emulsifier: 0.3 parts by weight of alkylarylpolyglycolether

To produce a suitable preparation of active compound, 1 part by weight of active compound is mixed with the stated amounts of solvent and emulsifier, and the concentrate is diluted with water to the desired concentration.

To test for curative activity, young plants are inoculated with an aqueous spore suspension of *Phytophthora infestans*. The plants remain in an incubation cabinet at 20° C. and 100% relative atmospheric humidity for 7 hours. After a short drying-off time, the plants are sprayed with the preparation of active compound until dripping wet.

The plants are placed in an incubation cabin at 100% relative atmospheric humidity and at about 20° C.

Evaluation is carried out 3 days after the inoculation.

The active compounds, active compound concentrations and results can be seen from the following table.

TABLE B

Phytophthora test (tomato)/curative

| Active compound | Infestation in % at an active compound concentration of 100 ppm |
|---|---|
| known: | |
| ![structure A] | 69 |
| According to the invention: | |
| (2) | 9 |

It will be understood that the specification and examples are illustrative but not limitative of the present invention and that other embodiments within the spirit and scope of the invention will suggest themselves to those skilled in the art.

What is claimed is:

1. A phenylsulphonylazole of the formula

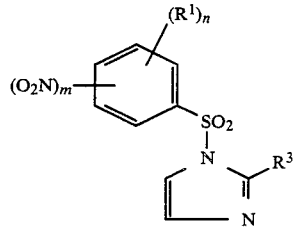

in which
R$^1$ is alkyl with 1 to 6 carbon atoms,
m is 1 or 2,
n is 0 or 1, and
R$^3$ is alkyl with 1 to 4 carbon atoms.

2. A compound according to claim 1, in which
R$^1$ is methyl, ethyl or n-propyl, and
R$^3$ is methyl.

3. A compound according to claim 1, of the formula

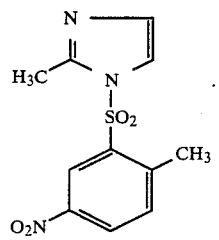

4. A fungicidal composition comprising a fungicidally effective amount of a phenylsulphonyl azole of the formula

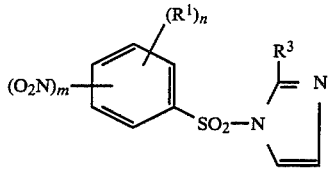

in which

R¹ is alkyl with 1 to 6 carbon atoms, m is 1 or 2, n is 0 or 1, and

R³ is alkyl with 1 to 4 carbon atoms in admixture with a diluent or carrier.

5. A composition according to claim 4, in which R¹ is methyl, ethyl or n-propyl.

6. A composition according to claim 4, wherein the azole is of the formula

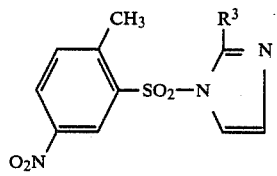

7. A composition according to claim 4, wherein the azole is of the formula

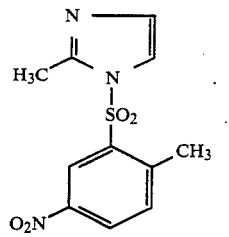

8. A method of combating fungi which comprises applying to the fungi or to their habitat a fungicidally effective amount of a phenylsulphonyl azole of the formula

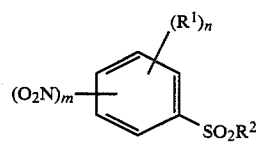

in which

R¹ is alkyl with 1 to 6 carbon atoms,
m is 1 or 2,
n is 0 or 1, and
R³ is alkyl with 1 to 4 carbon atoms.

9. The method according to claim 8, wherein the azole is of the formula

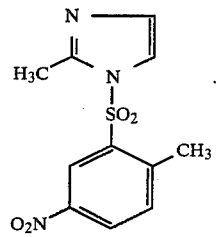

10. The method according to claim 8, wherein the azole is applied in a concentration of 1 to 0.001% by weight.

* * * * *